(12) United States Patent
Song et al.

(10) Patent No.: US 11,009,496 B2
(45) Date of Patent: May 18, 2021

(54) METHOD AND APPARATUS FOR DETERMINING STRUCTURES USING METAL PAIRS

(71) Applicant: SAMSUNG ELECTRONICS CO., LTD., Suwon-si (KR)

(72) Inventors: You Young Song, Yongin-si (KR); Kyoung Min Min, Seoul (KR); Seung-Woo Seo, Suwon-si (KR); Eun Seog Cho, Yongin-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 388 days.

(21) Appl. No.: 15/603,017

(22) Filed: May 23, 2017

(65) Prior Publication Data

US 2017/0343525 A1    Nov. 30, 2017

(30) Foreign Application Priority Data

May 24, 2016   (KR) .................. 10-2016-0063469

(51) Int. Cl.
*G01N 31/00*    (2006.01)
*G01N 33/20*    (2019.01)
*G16C 60/00*    (2019.01)
*G16C 10/00*    (2019.01)

(52) U.S. Cl.
CPC ............. *G01N 33/20* (2013.01); *G16C 60/00* (2019.02); *G16C 10/00* (2019.02)

(58) Field of Classification Search
None
See application file for complete search history.

(56) References Cited

U.S. PATENT DOCUMENTS

| 6,380,553 | B2 | 4/2002 | Gudesen et al. | |
|---|---|---|---|---|
| 9,627,717 | B1 * | 4/2017 | Langlois | ............... H01M 6/188 |
| 2009/0157369 | A1 * | 6/2009 | Li | ........... G16C 60/00 |
| | | | | 703/12 |
| 2011/0066414 | A1 | 3/2011 | Mills | |
| 2012/0130690 | A1 | 5/2012 | Srivastava et al. | |

(Continued)

FOREIGN PATENT DOCUMENTS

| KR | 1020150064602 |   | 6/2015 | |
|---|---|---|---|---|
| KR | 10-2017-0040019 | * | 10/2017 | ............. C30B 29/26 |
| WO | 2007071095 |   | 6/2007 | |

OTHER PUBLICATIONS

Brett Ammundsen, et al., "Lattice Dynamics and Vibrational Spectra of Lithium Manganese Oxides: A Computer Simulation and Spectroscopic Study", J. Phys. Chem. B, (1999), vol. 103, pp. 5175-5180.

(Continued)

*Primary Examiner* — Aditya S Bhat
(74) *Attorney, Agent, or Firm* — Cantor Colburn LLP

(57) ABSTRACT

An exemplary embodiment provides a method of determining formation energy of a multi-element crystal, including: generating information related to a candidate structure of the multi-element crystal and information related to a metal pair included in the multi-element crystal, based on information related to a composition of the multi-element crystal; and determining the formation energy based on the information related to the candidate structure and the information related to the metal pair.

20 Claims, 6 Drawing Sheets

(a)        (b)

(56) References Cited

U.S. PATENT DOCUMENTS

| | | | |
|---|---|---|---|
| 2012/0130692 A1 | 5/2012 | Li et al. | |
| 2012/0330632 A1 | 12/2012 | Oganov et al. | |
| 2015/0154146 A1 | 6/2015 | Yoo et al. | |
| 2017/0097310 A1* | 4/2017 | Song | G06F 30/20 |
| 2018/0219554 A1* | 8/2018 | Kobayashi | G02B 27/0955 |

OTHER PUBLICATIONS

Dipta Bhanu Ghosh, et al., "Structural phase transition path-following and stable phase scouting through a coupled DFT-BFB algorithm", Modelling and Simulation in Materials Science and Engineering, (2011), vol. 19, No. 8, pp. 1-12.

Duho Kim, et al., "Structural Stability and Electrochemical Properties of Over-Lithiated Oxide from Ab initio Predictive Comparative Study", The Korean Society of Mechanical Engineers, (Dec. 2013), pp. 1544-1548.

James E. Saal, et al., "Materials Design and Discovery with High-Throughput Density Functional Theory: The Open Quantum Materials Database (OQMD)", The Minerals, Metals & Materials Society, (2013), vol. 65, No. 11, pp. 1501-1509.

Ronald Michalsky, et al., "Design Principles for Metal Oxide Redox Materials for Solar-Driven Isothermal Fuel Production", Adv. Energy Mater., (2015), vol. 5, pp. 1-10.

Ruijuan Xiao, et al., "High-throughput design and optimization of fast lithium ion conductors by the combination of bond-valence method and density functional theory", Scientific Reports, (2015), vol. 5, No. 14227, pp. 1-11.

Ying Shirley Meng, et al., "First principles computational materials design for energy storage materials in lithium ion batteries", Energy Environ. Sci., (2009), vol. 2, pp. 589-609.

* cited by examiner (a)           (b)

METHOD AND APPARATUS FOR DETERMINING STRUCTURES USING METAL PAIRS

CROSS-REFERENCE TO RELATED APPLICATION

This application claims priority to Korean Patent Application No. 10-2016-0063469 filed on May 24, 2016, and all the benefits accruing therefrom under 35 U.S.C. § 119, the content of which in its entirety is herein incorporated by reference.

BACKGROUND

(a) Field

The disclosure relates to a method and an apparatus for determining a stable structure of multi-element crystal.

(b) Description of the Related Art

A method for finding a stable structure of a crystal system may use density functional theory ("DFT"). The DFT is one of theories for calculating forms and energy of electrons positioned in a material or molecules based on quantum mechanics. However, the DFT typically takes a long time to calculate a structure so the DFT may be restrictively used for a case with several candidate structures. For example, multi-element cathode materials such as a lithium nickel cobalt manganese oxide ($LiNi_xCo_yMn_{1-x-y}O_2$, NCM) or a lithium nickel cobalt aluminum oxide ($LiNi_xCo_yAl_{1-x-y}O_2$, NCA) may have several thousands to several tens of thousands of candidate structures depending on structures or compositions, so the DFT may not be effectively applied to such a case.

Accordingly, methods of estimating a crystal structure by using the DFT and an algorithm complementary to the DFT have been researched. As one of such methods, a method of utilizing a local order matrix, which is a method of representing atomic arrangement in a structure in addition to the DFT, has been suggested. According to the method of utilizing a local order matrix with the DFT, a plurality of candidate structures are classified by using the local order matrix, but it may be difficult to detect a stable structure in view of energy. For example, in such a method, all possible candidate structures of a specific material may be generated, then a local order matrix may be generated based on the number of the transition metals that are adjacent to each other in the candidate structures, and the candidate structures may be grouped based on the local order matrix. However, conventionally, no method of selecting a representative structure of the structures included in each group has been suggested, while lattice sizes and energies of two different structures have been shown.

SUMMARY

In a method of utilizing a local order matrix, which is a method of representing atomic arrangement in a structure in addition to density functional theory ("DFT"), a structure determining technique is desired to cover the cases of many various candidate structures with complex DFT calculation caused by a large number of atoms in each structure.

Exemplary embodiments relate to a method of determining formation energy based on information related to candidate structures of a multi-element crystal and determining information related to metal pairs included in the multi-element crystal, to quickly determine the formation energy even when the multi-element crystal includes many various candidate structures or the number of atoms included in the multi-element crystal is relatively great.

Exemplary embodiments relate to an apparatus for determining formation energy based on information related to candidate structures of a multi-element crystal and information related to metal pairs included in the multi-element crystal.

An exemplary embodiment provides a method of determining formation energy of a multi-element crystal. In such an embodiment, the formation energy determining method includes: generating information related to a candidate structure of the multi-element crystal and information related to a metal pair included in the multi-element crystal, based on information related to a composition of the multi-element crystal; and determining the formation energy based on the information related to the candidate structure and the information related to the metal pair.

In an exemplary embodiment, the information related to the metal pair may include kinds of the metal pair, a number of the metal pair for each kind thereof, and metal pair energy for each kind thereof.

In an exemplary embodiment, the determining the formation energy may include calculating the formation energy based on a multiplication of the number of the metal pair and the metal pair energy for each kind thereof.

In an exemplary embodiment, the calculating the formation energy based on the multiplication of the number of the metal pair and the metal pair energy for each kind thereof may include: calculating formation energy of the candidate structure based on information related to the candidate structure by using a quantum chemical computer simulation method; and estimating the metal pair energy based on energy of the candidate structure and the number of the metal pair for each kind thereof.

In an exemplary embodiment, the multi-element crystal includes a relatively large number of atoms, and the estimating the metal pair energy may include: dividing the candidate structure of the multi-element crystal into a plurality of sub-structures; and estimating the metal pair energy based on energy of the sub-structures and the number of the metal pair for each kind thereof.

In an exemplary embodiment, the estimating the metal pair energy may include verifying the estimated metal pair energy for the candidate structure based on formation energy determined based on the metal pair energy and formation energy calculated by using the quantum chemical computer simulation method.

In an exemplary embodiment, the multi-element crystal may include n kinds of metal pairs, and the calculating the formation energy of the candidate structure by using the quantum chemical computer simulation method may include calculating formation energies of n or more of the candidate structures of the multi-element crystal.

In an exemplary embodiment, the calculating the formation energies of n or more of the candidate structures of the multi-element crystal may include grouping the candidate structures based on the number of the metal pair for each kind thereof and selecting at least one from among each of grouped candidate structure groups.

In an exemplary embodiment, the calculating the formation energies of n or more of the candidate structures of the multi-element crystal may include grouping the candidate structures based on a composition of the multi-element crystal and selecting at least one from among each of grouped candidate structure groups.

In an exemplary embodiment, the formation energy determining method may further include: determining a stable composition of the multi-element crystal including the most stable structure based on the formation energy; calculating the formation energy for all candidate structures included in the composition, based on a multiplication of the number of the metal pair and the metal pair energy for each kind thereof; and determining a candidate structure including the lowest formation energy among all the candidate structures included in the composition as the most stable structure.

In an exemplary embodiment, the formation energy determining method may further include storing the information related to the candidate structure and the information related to the metal pair in a database.

An exemplary embodiment provides an apparatus of determining formation energy of a multi-element crystal. In such an embodiment, the formation energy determining apparatus includes a processor and a memory connected to the processor, where the processor executes a program stored in the memory to perform: generating information related to a candidate structure of the multi-element crystal and information related to a metal pair included in the multi-element crystal, based on information related to a composition of the multi-element crystal, and determining the formation energy based on the information related to the candidate structure and the information related to the metal pair.

In an exemplary embodiment, the information related to the metal pair may include kinds of the metal pair, a number of the metal pair for each kind thereof, and the metal pair energy for each kind thereof.

In an exemplary embodiment, the processor may perform the calculating the formation energy by calculating the formation energy based on a multiplication of the number of the metal pair and the metal pair energy for each kind thereof.

In an exemplary embodiment, the processor may perform the calculating the formation energy based on the multiplication of the number of the metal pair and the metal pair energy for each kind thereof, by calculating formation energy of the candidate structure based on information related to the candidate structure by using a quantum chemical computer simulation method, and estimating the metal pair energy based on energy of the candidate structure and the number of the metal pair for each kind thereof.

In an exemplary embodiment, the multi-element crystal may include a relatively large number of atoms, and the processor may perform the estimating the metal pair energy by dividing the candidate structure of the multi-element crystal into a plurality of sub-structures, and estimating the metal pair energy based on energy of the sub-structures and the number of the metal pair for each kind thereof.

In an exemplary embodiment, the processor may perform the estimating the metal pair energy by verifying the estimated metal pair energy for the candidate structure based on formation energy determined based on the metal pair energy and formation energy calculated by using the quantum chemical computer simulation method.

In an exemplary embodiment, the multi-element crystal may include n kinds of metal pair, and the processor may perform the calculating the formation energy of the candidate structure through the quantum chemical computer simulation method by calculating formation energies of n or more of the candidate structures of the multi-element crystal.

In an exemplary embodiment, the processor may perform the calculating the formation energies of n or more of the candidate structures of the multi-element crystal by grouping the candidate structures based on the number of the metal pair for each kind thereof and selecting at least one from among each of grouped candidate structure groups.

In an exemplary embodiment, the processor may perform the calculating the formation energies of n or more of the candidate structures of the multi-element crystal by grouping the candidate structures based on a composition of the multi-element crystal and selecting at least one from among each of grouped candidate structure groups.

In an exemplary embodiment, the processor may further perform: determining a stable composition of the multi-element crystal including the most stable structure based on the formation energy; calculating the formation energy for all candidate structures included in the composition, based on a multiplication of the number of the metal pair and the metal pair energy for each kind thereof; and determining a candidate structure including the lowest formation energy among all the candidate structures included in the composition as the most stable structure.

In an exemplary embodiment, the processor may further perform storing the information related to the candidate structure and the information related to the metal pair in a database.

According to exemplary embodiments, the formation energy of the multi-element crystal may be quickly estimated based on arrangement and energy of metal pairs, each indicating two metals that are adjacently disposed even when the multi-element crystal includes a relatively large number of atoms, such that the most stable one among candidate structures of the multi-element crystal may be quickly determined.

BRIEF DESCRIPTION OF THE DRAWINGS

These and/or other features of the invention will become apparent and more readily appreciated from the following detailed description of embodiments thereof, taken in conjunction with the accompanying drawings, in which.

DETAILED DESCRIPTION

Figure 1:
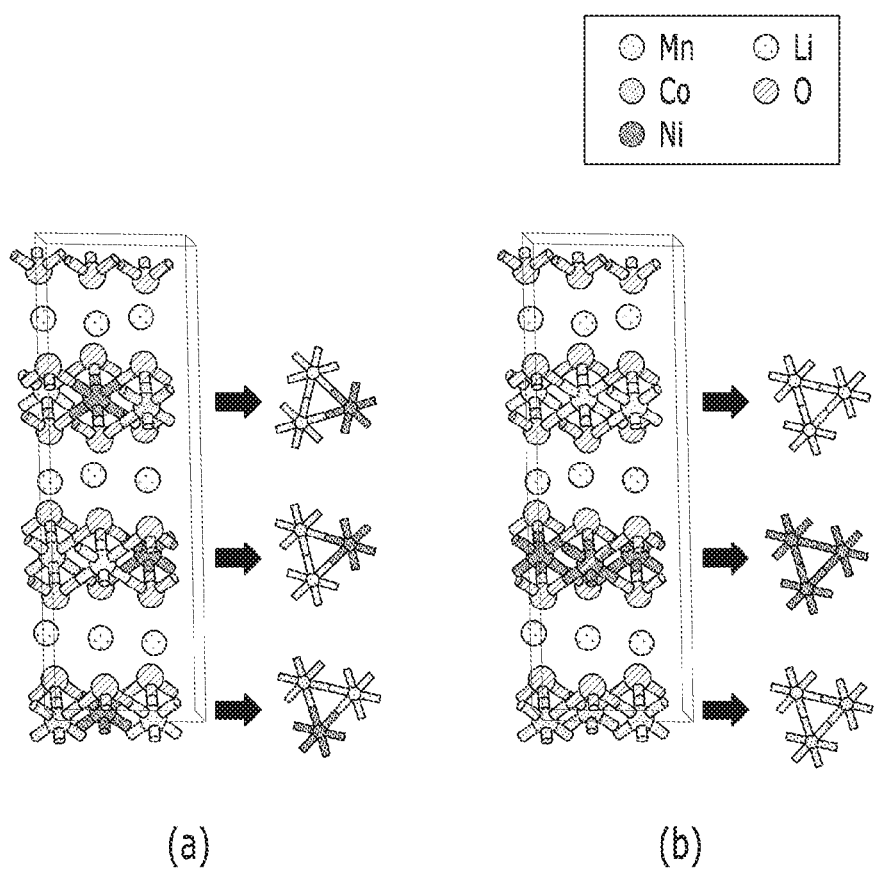
FIG. 1 is a schematic view illustrating a structure of a multi-element crystal NCM111 according to an exemplary embodiment.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive, and like reference numerals designate like elements throughout the specification.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 is a schematic view illustrating a structure of a multi-element crystal NCM111 according to an exemplary embodiment.

A multi-element crystal may be formed of various components of elements, and various candidate structures may exist according to each component. A lithium nickel-cobalt-manganese oxide (LiNi$_x$Co$_y$Mn$_{1-x-y}$O$_2$, NCM), for example, may include various compositions such as NCM111 (LiNi$_{1/3}$Co$_{1/3}$Mn$_{1/3}$O$_2$) and NCM522 (LiNi$_{5/9}$Co$_{2/9}$Mn$_{2/9}$O$_2$) depending on abundances of nickel (Ni), cobalt (Co), and manganese (Mn). Further, a frame of a structure is determined depending on each composition, and a candidate structure may be determined depending on a position of the frame of elements (e.g., Ni, Co, and Mn) included in the multi-element crystal. As result, when a composition and a frame of the multi-element crystal are the same in the candidate structures, the candidate structures of the multi-element crystal may be divided depending on positions of elements of the frame.

FIG. 1(a) and FIG. 1(b) show candidate structures of NCM111 (LiNi$_{1/3}$Co$_{1/3}$Mn$_{1/3}$O$_2$) of NCMs including 9 transition metals. Each of the candidate structures includes three transition metal layers including transition metals to which oxygen is coupled, and three lithium layers. In this case, in a first candidate structure of the NCM111 shown in FIG. 1(a), Ni, Co and Mn are respectively included in each of the transition metal layers, and in a second candidate structure shown in FIG. 1(b), one of Ni, Co and Mn is included in each of the transition metal layers. In this case, the transition metals have major influences on formation energy among elements included in the multi-element crystal.

Figure 2:
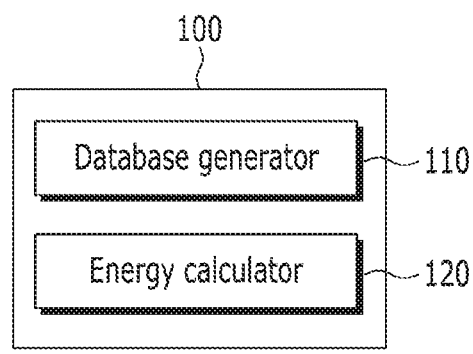
FIG. 2 is a block diagram illustrating a formation energy determining apparatus for determining formation energy of a multi-element crystal according to an exemplary embodiment.
Figure 3:
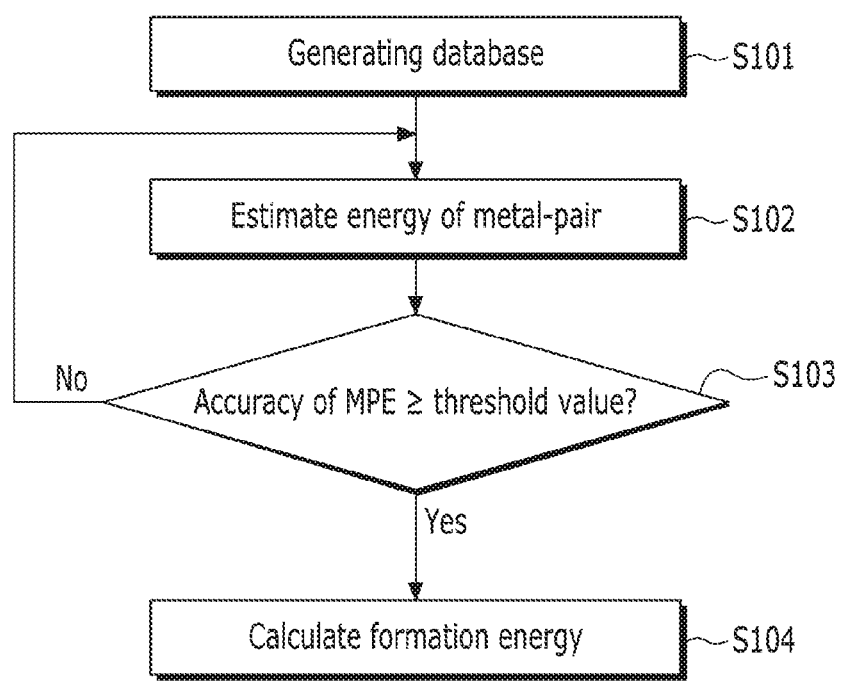
FIG. 3 is a flowchart illustrating a method of determining formation energy of a multi-element crystal according to an exemplary embodiment.

FIG. 2 is block diagram illustrating a formation energy determining apparatus for determining formation energy of a multi-element crystal according to an exemplary embodiment, and FIG. 3 is a flowchart illustrating a method of determining formation energy of a multi-element crystal according to an exemplary embodiment.

According to an exemplary embodiment, formation energy of the multi-element crystal may be determined based on the number of a metal pair (MP) indicating two metals adjacently disposed in the multi-element crystal and metal pair energy (MPE) of the metal pair. In such an embodiment, a pair of metals (or the metal pair) that are adjacently disposed or disposed closest to each other is denoted by MP$_{AB}$, and metal pair energy is denoted by MPE$_{AB}$. Equation 1 represents formation energy FE$_{crystal}$ of the multi-element crystal according to an exemplary embodiment.

$$FE_{crystal} = \sum_{ij} N_{ij} \times MPE_{ij} \qquad \text{(Equation 1)}$$

In Equation 1, N$_{ij}$ denotes the number of metal pairs MP$_{ij}$ for a kind thereof, and MPE$_{ij}$ denotes energy of the metal pair MP$_{ij}$. As a result, formation energy of the multi-element crystal may be represented by entirely summing a multiplication of the number of metal pairs and the metal pair energy for each kind thereof. Further, it may be assumed that a formation energy difference between the candidate structures of the multi-element crystal is caused by arrangement of the metal pairs. MP structures, in which two candidate structures are the same, indicate that kinds and numbers of MPs included in the multi-element crystal are the same. In an exemplary embodiment, candidate structures in which the kinds and numbers of MPs are different indicate different MP structures even if compositions thereof are the same as each other.

Referring to FIG. 2, an exemplary embodiment of the formation energy determining apparatus 100 includes a database generator 110 and an energy calculator 120.

In such an embodiment, when information related to a composition of a multi-element crystal is received from a user, the database generator 120 generates a database to be used to calculate energy of the multi-element crystal or candidate structures of the multi-element crystal (hereinafter, simply referred to as 'database'). In such an embodiment, the database may include information related to candidate structures of the multi-element crystal and information related to metal pairs of the multi-element crystal. The information related to the metal pairs includes kinds of metal pairs, the number of metal pairs per kind, and metal pair energy.

The energy calculator 120 calculates formation energy of a specific candidate structure, and determines the most stable one of the candidate structures of the multi-element crystal based on the calculated formation energy of the candidate structures. The energy calculator 120 may calculate formation energy of a specific candidate structure of the multi-element crystal by using Equation 1, and may determine the most stable one based on formation energy of each candidate structure. A method of calculating the formation energy of the specific candidate structure and a method of determining the most stable structure by the energy calculator 120 will hereinafter be described in detail with reference to FIG. 3.

Referring to FIG. 3, the database generator 110 generates a database based on information related to composition of the multi-element crystal, received from a user (S101). In an exemplary embodiment, the information related to the composition of the multi-element crystal, inputted by the user, includes a combination of a chemical formula of the multi-element crystal and information related to space groups of elements included in the multi-element crystal, or information of coordinates of each element included in the multi-element crystal.

In such an embodiment, a kind of the metal pair may be determined depending on a kind of a major element, and a major element of the multi-element crystal may be determined based on composition of the multi-element crystal. In one exemplary embodiment, for example, where a chemical formula of NCM111 is $LiNi_{1/3}Co_{1/3}Mn_{1/3}O_2$, major elements of NCM111 are Ni, Co, and Mn, which are transition metals, and the metal pairs that may be determined depending on such three kinds of transition metals are 6 kinds (Ni—Ni, Co—Co, Mn—Mn, Ni—Co, Co—Mn, and Mn—Ni). As a result, when the number of major elements of the multi-element crystal is n (here, n is a natural number), kinds of the metal pairs may be determined by using a formula for combinations with repetition as shown in Equation 2.

$$H(n, 2) = c(n + 2 - 1, 2) = \frac{n(n+1)}{2} \quad \text{(Equation 2)}$$

In such an embodiment, the number of the metal pairs may be determined depending on candidate structures. Referring back to FIG. 1(a), one transition metal layer included in a first candidate structure includes one metal pair $MP_{MnCo}$, one metal pair $MP_{CoNi}$, and one metal pair $MP_{NiMn}$. Since the number of transition metal layers is 3, the number of metal pairs included in the first candidate structure is 3. Accordingly, formation energy of the first candidate structure of NCM111 may be determined by using Equation 3.

$$FE_{NCM_1} = \sum_{ij} N_{ij} \times MPE_{ij} = \quad \text{(Equation 3)}$$
$$N_{MnCo}MPE_{MnCo} + N_{CoNi}MPE_{CoNi} + N_{NiMn}MPE_{NiMn} =$$
$$3MPE_{MnCo} + 3MPE_{CoNi} + 3MPE_{NiMn}$$

Further, referring to FIG. 1(b), each transition metal layer of a second candidate structure includes only one of Ni, Co, and Mn, and thus three metal pairs $MP_{MnMn}$, $MP_{CoCo}$, and $MP_{NiNi}$ are included in the transition metal layers, respectively. Accordingly, formation energy of the second candidate structure of NCM111 may be determined by using Equation 4.

$$FE_{NCM_2} = \sum_{ij} N_{ij} \times MPE_{ij} = \quad \text{(Equation 4)}$$
$$N_{MnMn}MPE_{MnMn} + N_{CoCo}MPE_{CoCo} + N_{NiNi}MPE_{NiNi} =$$
$$3MPE_{MnMn} + 3MPE_{CoCo} + 3MPE_{NiNi}$$

According to an exemplary embodiment, the energy calculator 120 statistically calculates metal pair energy MPE based on information related to the metal pairs and information related to the candidate structures included in the database. In such an embodiment, the energy calculator 120 verifies accuracy of the calculated metal pair energy, and calculates formation energy of a specific candidate structure by using Equation 1 based on kinds of the metal pairs included in the specific candidate structure, the number of the metal pair per kind, and the metal pair energy corresponding thereto.

The energy calculator 120 calculates formation energy of a candidate structure by applying an ab initio formation energy calculating method based on Equation 5, and estimates metal pair energy by substituting it with a left side of Equation 1 (S102).

$$FE_{NCM} = \frac{E_{NCM} - \sum N_X E_X}{\sum N_X} \quad \text{(Equation 5)}$$

Equation 5 indicates a DFT method of the ab initio formation energy calculating method. In Equation 5, X may be lithium (Li), oxygen (O), Ni, Co, or Mn, which is included in an NCM crystal, $N_X$ denotes the number of X included in the candidate structure, and $E_{NCM}$ and $E_X$ respectively denote total energy of the NCM structure and energy of the X. In general, the formation energy of the candidate structure of the multi-element crystal may be determined based on energy of the candidate structure, e.g., by subtracting energy of each atom included in the candidate structure from the total energy of the candidate structure.

In such an embodiment, the formation energies of the first and second candidate structures calculated by using Equation 5 may be respectively −1.54 and −1.48. As a result, the first candidate structure has lower energy than that of the second candidate structure. However, when formation energies of all candidate structures are calculated by using the DFT method, a lot of time is consumed due to an excessive calculation amount, or when a relatively large number (e.g., 500 or more) of atoms are included in the candidate structure, the formation energy may not be effectively calculated by using the DFT method. According to an exemplary embodiment, the energy calculator 120 uses formation energy of the candidate structure calculated by using DFT theory to calculate metal pair energy thereof. In Equation 4 and Equation 5, left sides thereof may be calculated by using the DFT theory such as Equation 1, and terms related to metal pair energy at right sides are unknown. As a result, Equation 6 may be used to calculate MPE.

$$FE_{NCM} = \frac{E_{NCM} - \sum N_X E_X}{\sum N_X} = \sum_{ij} N_{ij} \times MPE_{ij} \quad \text{(Equation 6)}$$

Equation 6 is obtained by combining Equation 1 and Equation 5. Equation 5 is related to the formation energy of the multi-element crystal calculated by using the DFT theory, and Equation 1 is related to the formation energy of the multi-element crystal calculated by using a formation energy determining method according to an exemplary embodiment. Accordingly, when the number of metal pairs is determined depending on the candidate structure of the multi-element crystal, the energy calculator 120 may estimate MPE by using Equation 6. According to an exemplary embodiment, a quantum chemical computer simulation method such as a pseudopotential method or a total energy development method may be used to the left side of Equation 1, in addition to the DFT theory.

In such an embodiment, since MPE is used for each metal pair of the multi-element crystal, the number of MPEs to be calculated for one multi-element crystal is the same as the number of kinds of the metal pairs. In one exemplary embodiment, for example, where the metal pairs included in NCM111 are 6 kinds, the number of MPEs to be calculated is 6. In an exemplary embodiment, the number of equations such as Equation 6 is equal to or greater than the number of MPEs to be calculated. In one exemplary embodiment, for example, in the case of NCM111, the number of MPEs to be calculated is 6, and thus 6 or more equations such as Equation 6 are used. Equation 7 may be used for estimating MPE.

$$\begin{pmatrix} MPE_{ij} \\ \vdots \end{pmatrix} = \begin{pmatrix} N_{ij} & \cdots \\ \vdots & \ddots \end{pmatrix}^{-1} \begin{pmatrix} FE_{crystal} \\ \vdots \end{pmatrix} \quad \text{(Equation 7)}$$

In Equation 7, the number of rows of each matrix is equal to the number of MPEs to be calculated.

The energy calculator 120 may select some candidate structures (the number of which is equal to or greater than the number of MPEs to be calculated), and may apply the DFT theory to calculate formation energies of the selected candidate structures. In one exemplary embodiment, for example, a total number of candidate structures of NCM111 is 1680 ($_9C_3 \times _6C_3 \times _3C_3$), and formation energies of some candidate structures among them may be used to estimate MPE. A total number of candidate structures of NCM522 (LiNi$_{5/9}$CO$_{2/9}$Mn$_{2/9}$O$_2$) is 756 ($_9C_5 \times _4C_2 \times _2C_2$), and Table 1 shows the number of MPs for each composition of NCM.

According to an exemplary embodiment, the energy calculator 120 may select candidate structures to calculate MPE based on classifications of the multi-element crystal, as shown in Table 1.

Referring to Table 1, in the case of calculating formation energies of the candidate structures of NCM111, for example, candidate structures for estimating MPE may be selected from first candidate structure groups other than second candidate structure groups in which the numbers of the metal pairs MP$_{MnMn}$, MP$_{CoCo}$, MP$_{NiNi}$, MP$_{MnCo}$, MP$_{CoNi}$ and MP$_{NiMn}$ are respectively 0, 0, 0, 9, 9 and 9, or 9, 9, 9, 0, 0 and 0, among 9 candidate structure groups of NCM111. As a result, the candidate structures of NCM111 may be grouped based on the number of MPs for each kind. According to an exemplary embodiment, the number of MPEs to be calculated in NCM is 6, and thus at least one candidate structure may be selected from each candidate structure group grouped based on the number of MPs for each kind.

In one alternative exemplary embodiment, for example, in the case of estimating MPE to determine the most stable one of the candidate structures of the multi-element crystal NCM, the candidate structures may be grouped based on compositions of NCM. When the number of MPEs to be calculated in NCM is 6, at least one candidate structure may be selected from each candidate structure group grouped depending on the compositions of NCM.

In an exemplary embodiment, the energy calculator 120 calculates first formation energy of a candidate structure included in a database based on the estimated MPE, and verifies accuracy of the estimated MPE by comparing the formation energy calculated based on the estimated MPE with second formation energy calculated based on the DFT theory (S103). In one exemplary embodiment, for example, $R^2$ (R-squared) may be used to verify the accuracy of the estimated MPE. According to an exemplary embodiment, when $R^2$ is smaller than 0.9, for example, the energy calculator 120 calculates formation energy of another candidate structure included in the database through the DFT theory, and re-estimates MPE depending on Equation 6 and Equation 7. As a result, the energy calculator 120 may repeatedly verify the accuracy of the estimated MPE until $R^2$ is equal to or greater than a predetermined threshold value (e.g., 0.9). In such an embodiment, the threshold value for $R^2$ may be predetermined. Table 2 shows MPE estimated based on six candidate structures, MPE estimated based on 202 candidate structures, and $R^2$ for each case.

TABLE 1

| NCM Composition | Number of candidate structures | $N_{MnMn}$ | $N_{CoCo}$ | $N_{NiNi}$ | $N_{MnCo}$ | $N_{MnNi}$ | $N_{NiCo}$ |
|---|---|---|---|---|---|---|---|
| NCM111 | 1680 | 0 | 0 | 0 | 9 | 9 | 9 |
| | | 0 | 3 | 3 | 9 | 9 | 3 |
| | | 3 | 0 | 3 | 9 | 3 | 9 |
| | | 3 | 3 | 0 | 3 | 9 | 9 |
| | | 3 | 3 | 3 | 6 | 6 | 6 |
| | | 9 | 3 | 3 | 0 | 0 | 12 |
| | | 3 | 9 | 3 | 0 | 12 | 0 |
| | | 3 | 3 | 9 | 12 | 0 | 0 |
| | | 9 | 9 | 9 | 0 | 0 | 0 |
| NCM522 | 756 | 0 | 0 | 6 | 3 | 9 | 9 |
| | | 3 | 0 | 6 | 0 | 6 | 12 |
| | | 0 | 3 | 6 | 0 | 12 | 6 |
| | | 0 | 0 | 9 | 6 | 6 | 6 |
| | | 0 | 3 | 12 | 6 | 6 | 0 |
| | | 3 | 0 | 12 | 6 | 0 | 6 |
| | | 3 | 3 | 9 | 0 | 6 | 6 |
| NCM711 | 72 | 0 | 0 | 18 | 3 | 3 | 3 |
| | | 0 | 0 | 15 | 0 | 6 | 6 |
| NCM621 | 252 | 0 | 0 | 9 | 0 | 6 | 12 |
| | | 0 | 0 | 12 | 3 | 3 | 9 |
| | | 0 | 3 | 18 | 6 | 0 | 0 |
| | | 0 | 3 | 12 | 0 | 6 | 6 |
| NCM612 | 252 | 0 | 0 | 9 | 0 | 12 | 6 |
| | | 0 | 0 | 12 | 3 | 9 | 3 |
| | | 3 | 0 | 18 | 6 | 0 | 0 |
| | | 3 | 0 | 12 | 0 | 6 | 6 |

TABLE 2

| MP | MPE 6 | MPE 202 |
|---|---|---|
| MM | −0.067 | −0.067 |
| CC | −0.052 | −0.052 |
| NN | −0.045 | −0.044 |
| MC | −0.061 | −0.061 |
| MN | −0.059 | −0.059 |
| NC | −0.050 | −0.049 |
| $R^2$ | 0.985 | 0.986 |

Referring to Table 2, MPEs of each MP estimated based on the six candidate structures are substantially the same as MPEs estimated based on 202 candidate structures. In other words, MPE may be very quickly determined by calculating formation energy of minimum candidate structures used to estimate MPE through a DFT.

When the accuracy of the estimated MPE is verified, the energy calculator 120 determines formation energy of a specific candidate structure by using Equation 1 (S104).

Conventionally, when the multi-element crystal includes a relatively large number (e.g., 500 or more) of atoms, it may be difficult to apply the DFT theory. In an exemplary embodiment, however, it is possible to effectively apply the formation energy determining method. When the multi-element crystal includes a relatively large number of atoms, the database generator 110 generates a database by dividing one candidate structure into a plurality of sub-structures. Then, the energy calculator 120 may estimate and verify MPE by using energies of the sub-structures to determine formation energy of the candidate structure.

Figure 4:
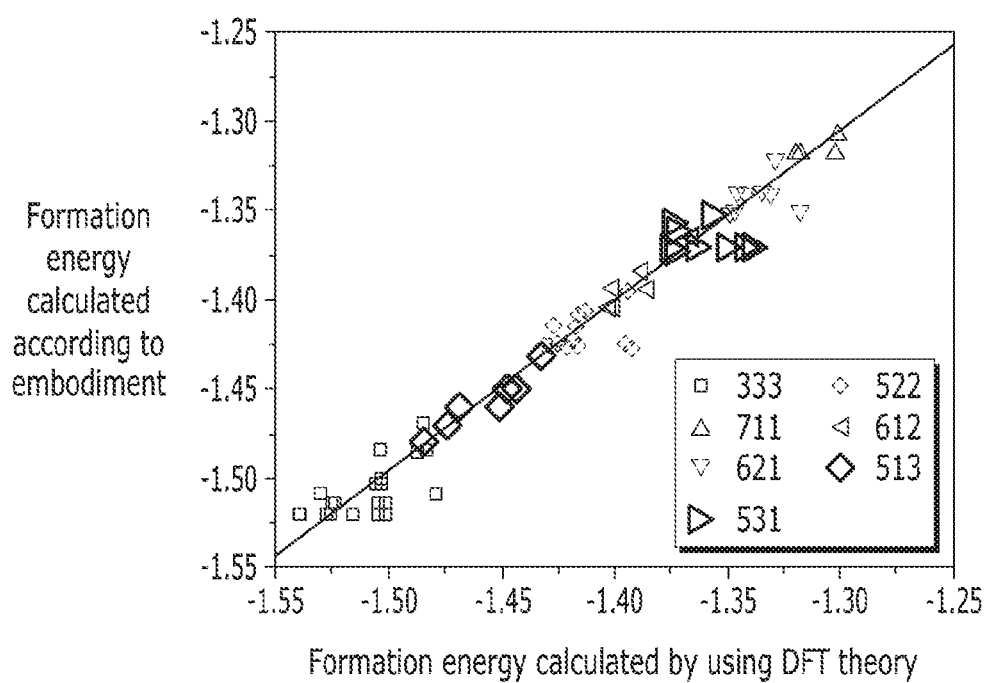
FIG. 4 is a graph illustrating formation energy distribution of an NCM including 9 transition metals according to an exemplary embodiment.
Figure 5:
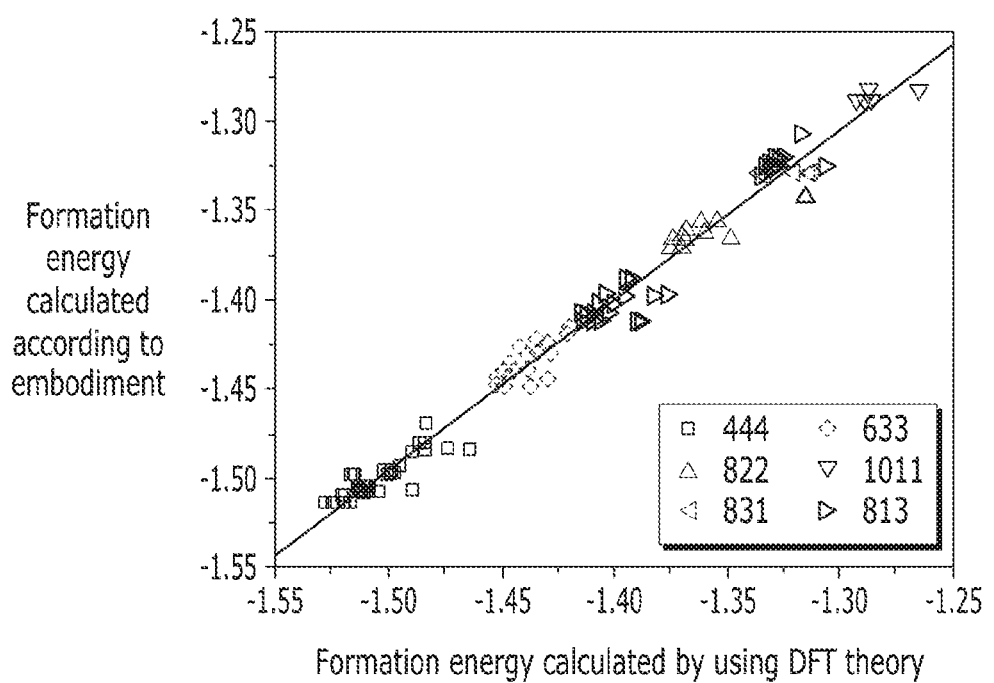
FIG. 5 is a graph illustrating formation energy distribution of an NCM including 12 transition metals according to an exemplary embodiment.

FIG. 4 is a graph illustrating formation energy distribution of an NCM including 9 transition metals according to an exemplary embodiment, and FIG. 5 is a graph illustrating formation energy distribution of an NCM including 12 transition metals according to an exemplary embodiment.

In FIG. 4 and FIG. 5, an x-axis indicates formation energy calculated through the DFT theory, and a y-axis indicates formation energy caused by the formation energy determining method. A straight line y=x diagonally traverses the graphs. Referring to FIG. 4 and FIG. 5, the formation energy calculated by using the formation energy determining method according to an exemplary embodiment is calculated to be substantially the same as the formation energy calculated by using the DFT theory.

FIG. 4 further shows that the formation energy of NCM333 is lowest in compositions of NCM including 9 transition metals, and FIG. 5 further shows that the formation energy of NCM444 is lowest in compositions of NCM including 12 transition metals. Accordingly, the energy calculator 120 may determine the most stable structure of the multi-element crystal by determining a composition of the multi-element crystal including a candidate structure having a lowest energy, and calculating energies of all candidate structures included in the composition based on Equation 1.

In an exemplary embodiment, in the case of the multi-element crystal NCM, for example, the structure including the most stable structure among a plurality of compositions is determined as NCM111 by using a small amount of calculation compared with the DFT theory. If the most stable structure is searched for the NCM including 9 transition metals based on the DFT theory, formation energy is used to be calculated for 4020 (60,192 in the case of the NCM 12 transition metals) NCM candidate structures. However, according to an exemplary embodiment, it is possible to efficiently and quickly determine the most stable structure compared with the DFT by quickly calculating formation energy of a composition determined as a composition including the most stable structure at an accuracy of 0.9 based on Equation 1.

As described above, in an exemplary embodiment, formation energy of multi-element crystal is quickly estimated even when the multi-element crystal includes a relatively large number of atoms based on arrangement and energy of metal pairs, each indicating two metals that are adjacently disposed, and thus, the most stable one among candidate structures of the multi-element crystal may be quickly determined.

Figure 6:
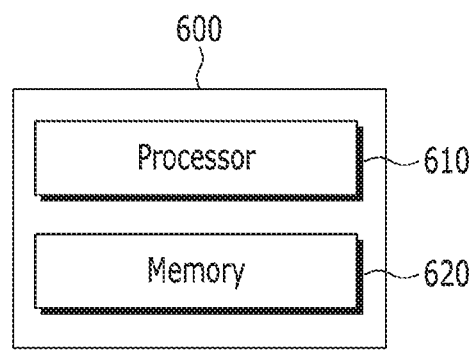
FIG. 6 is a block diagram illustrating a formation energy determining apparatus according to an alternative exemplary embodiment.

FIG. 6 is a block diagram illustrating a formation energy determining apparatus according to an alternative exemplary embodiment.

Referring to FIG. 6, an exemplary embodiment of the formation energy determining apparatus 600 includes a processor 610 and a memory 620.

The memory 620 may be connected with the processor 610 and store various information for driving the processor 610, or a program to be executed by the processor 610. The processor 610 may be configured to implement a function, a process or a method of exemplary embodiments set forth herein. An operation of the formation energy determining apparatus 600 may be implemented by the processor 610.

In an exemplary embodiment of the invention, the memory may be disposed at an interior or exterior of the processor, and may be connected to the processor by a means or element well-known in the art. The memory may be one of various volatile and non-volatile storing media. In one exemplary embodiment, for example, the memory may include a read-only memory ("ROM") or a random access memory ("RAM").

While the invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of determining formation energy of a multi-element crystal for determining a stable structure of the multi-element crystal using density functional theory, the method comprising:
generating information related to a candidate structure of the multi-element crystal and information related to a metal element pair included in the multi-element crystal, based on information related to a composition of the multi-element crystal; and
determining the formation energy based on the information related to the candidate structure and the information related to the metal element pair,
wherein the information related to the metal element pair comprises kinds of the metal element pair, a number of the metal element pair for each kind thereof, and metal element pair energy for each kind thereof.

2. The method of claim 1, wherein the determining the formation energy comprises calculating the formation energy based on a multiplication of the number of the metal element pair and the metal element pair energy for each kind thereof.

3. The method of claim 2, wherein the calculating the formation energy based on the multiplication of the number of the metal element pair and the metal element pair energy for each kind thereof comprises:
calculating formation energy of the candidate structure based on information related to the candidate structure by using a quantum chemical computer simulation method; and
estimating the metal element pair energy based on energy of the candidate structure and the number of the metal element pair for each kind thereof.

4. The method of claim 3, wherein
the multi-element crystal comprises a relatively large number of atoms, and
the estimating the metal element pair energy comprises:
dividing the candidate structure of the multi-element crystal into a plurality of sub-structures; and
estimating the metal element pair energy based on energy of the sub-structures and the number of the metal element pair for each kind thereof.

5. The method of claim 3, wherein the estimating the metal element pair energy comprises verifying the estimated metal element pair energy for the candidate structure based on formation energy determined based on the metal element pair energy and formation energy calculated by using the quantum chemical computer simulation method.

6. The method of claim 3, wherein,
the multi-element crystal includes n kinds of metal element pair, and
the calculating the formation energy of the candidate structure by using the quantum chemical computer simulation method comprise calculating formation energies of n or more of the candidate structures of the multi-element crystal.

7. The method of claim 6, wherein the calculating the formation energies of n or more of the candidate structures of the multi-element crystal comprises grouping the candidate structures based on the number of the metal element pair for each kind thereof and selecting at least one from among each of grouped candidate structure groups.

8. The method of claim 6, wherein the calculating the formation energies of n or more of the candidate structures of the multi-element crystal comprises grouping the candidate structures based on a composition of the multi-element crystal and selecting at least one from among each of grouped candidate structure groups.

9. The method of claim 2, further comprising:
determining a stable composition of the multi-element crystal including the most stable structure based on the formation energy;
calculating the formation energy for all candidate structures included in the composition based on the multiplication of the number of the metal element pair and the metal element pair energy for each kind thereof; and
determining a candidate structure including the lowest formation energy among all the candidate structures included in the composition as the most stable structure.

10. The method of claim 1, further comprising:
storing the information related to the candidate structure and the information related to the metal element pair in a database.

11. An apparatus which determines formation energy of a multi-element crystal for determining a stable structure of the multi-element crystal using density functional theory, the apparatus comprising:
a processor; and
a memory connected to the processor,
wherein the processor executes a program stored in the memory to perform:
generating information related to a candidate structure of the multi-element crystal and information related to a metal element pair included in the multi-element crystal, based on information related to a composition of the multi-element crystal; and
determining the formation energy based on the information related to the candidate structure and the information related to the metal element pair,
wherein the information related to the metal element pair includes kinds of the metal element pair, a number of the metal element pair for each kind thereof, and the metal element pair energy for each kind thereof.

12. The apparatus of claim 11, wherein
the processor performs the calculating the formation energy by calculating the formation energy based on a multiplication of the number of the metal element pair and the metal element pair energy for each kind thereof.

13. The apparatus of claim 12, wherein
the processor performs the calculating the formation energy based on the multiplication of the number of the metal element pair and the metal element pair energy for each kind thereof, by calculating formation energy of the candidate structure based on information related to the candidate structure by using a quantum chemical computer simulation method, and estimating the metal element pair energy based on energy of the candidate structure and the number of the metal element pair for each kind thereof.

14. The apparatus of claim 13, wherein,
the multi-element crystal comprises a relatively large number of atoms, and
the processor performs the estimating the metal element pair energy by dividing the candidate structure of the multi-element crystal into a plurality of sub-structures, and estimating the metal element pair energy based on energy of the sub-structures and the number of metal element pairs for each kind thereof.

15. The apparatus of claim 13, wherein
the processor performs the estimating the metal element pair energy by verifying the estimated metal element pair energy for the candidate structure based on formation energy determined based on the metal element pair energy and formation energy calculated by using the quantum chemical computer simulation method.

16. The apparatus of claim 13, wherein
the multi-element crystal includes n kinds of metal element pair, and
the processor performs the calculating the formation energy of the candidate structure by using the quantum chemical computer simulation method by calculating formation energies of n or more of the candidate structures of the multi-element crystal.

17. The apparatus of claim 16, wherein
the processor performs the calculating the formation energies of n or more of the candidate structures of the multi-element crystal by grouping the candidate structures based on the number of metal element pairs for each kind thereof and selecting at least one from among each of grouped candidate structure groups.

18. The apparatus of claim 16, wherein
the processor performs the calculating the formation energies of n or more of the candidate structures of the multi-element crystal by grouping the candidate structures based on a composition of the multi-element crystal and selecting at least one from among each of grouped candidate structure groups.

19. The apparatus of claim 12, wherein the processor further performs:
determining a stable composition of the multi-element crystal including the most stable structure based on the formation energy;
calculating the formation energy for all candidate structures included in the composition, based on a multiplication of the number of the metal element pair and the metal element pair energy for each kind thereof; and
determining a candidate structure including the lowest formation energy among all the candidate structures included in the composition as the most stable structure.

20. The apparatus of claim 11, wherein the processor further performs storing the information related to the candidate structure and the information related to the metal element pair in a database.

* * * * *